United States Patent [19]

Hyun

[11] Patent Number: 5,383,868
[45] Date of Patent: Jan. 24, 1995

[54] WOMAN'S SANITARY NAPKIN

[76] Inventor: Kwang H. Hyun, 13701 E. Bannon Dr., Cerritos, Calif. 90701

[21] Appl. No.: 79,088

[22] Filed: Jun. 17, 1993

[51] Int. Cl.6 .................................. A61F 13/15
[52] U.S. Cl. ............................ 604/385.1; 604/386
[58] Field of Search ............... 604/385.1, 386, 384, 604/378

[56] References Cited

U.S. PATENT DOCUMENTS

| | | |
|---|---|---|
| 2,331,355 | 10/1943 | Strongson . |
| 3,897,783 | 8/1975 | Ginocchio . |
| 4,023,571 | 5/1977 | Comerford et al. ............... 604/387 |
| 4,046,147 | 9/1977 | Berg ................................. 604/387 |
| 4,983,173 | 1/1991 | Patience et al. .................. 604/384 |
| 5,290,262 | 3/1994 | Vukos et al. ................... 604/385.1 |

*Primary Examiner*—Jerome L. Kruter
*Attorney, Agent, or Firm*—Erik M. Arnhem

[57] ABSTRACT

A sanitary napkin for absorbing and collecting a woman's menstrual liquids, includes an absorbent pad positionable against the woman's abdomen and the skin area between the thighs so as to overly the vaginal opening. A porous absorbent plug extends from one face of the pad so as to be insertable into the woman's vagina. Menstrual blood and associated secretions flow through the porous plug into the pad for collection and safe retention. A liquid impermeable covering entirely surrounds the pad, but not the plug, such that menstrual liquids are prevented from leaking out of the pad or coming in contact with the woman's skin.

1 Claim, 1 Drawing Sheet

WOMAN'S SANITARY NAPKIN

BACKGROUND AND SUMMARY OF THE INVENTION

This invention relates to a sanitary napkin usable by women for absorbing blood and other secretions that are discharged from the uterus during menstruation periods. Such menstruation periods reoccur on an approximately monthly basis according to the menstrual cycle.

Conventional sanitary napkins comprise a pad formed out of a coherent mass of cotton batting, said pad usually having a length of about eight inches, a width of about two and one half inches, and a thickness of about three fourth inch. The pad is positioned against the woman's skin, with a portion thereof extending between the woman's thighs and another portion extending upwardly along her abdomen. Menstrual blood is discharged from the woman's vagina into the pad, which absorbs and distributes the blood along the pad width and length dimension, up to the saturation point of the pad material.

The major surface of the cotton pad not in contact with the woman's skin is covered by a thin sheet of plastic for preventing flow of blood out of the pad interior space; the plastic sheet keeps the blood flow within the pad.

The entire surface of the pad is encapsulated within a porous gauze cloth, whose purpose is to prevent the liquid soaked pad from deteriorating or fragmenting. The cloth also at least partially prevents the blood-soaked cotton from contacting the woman's skin or pubic hairs so as to form undesired deposits of blood or cotton on the skin surface.

One problem with conventional sanitary napkins is that the gauze cloth covering may not always be fully effective for its intended purpose, such that blood and secretions can be deposited on the skin surface, with consequent possibility for infection.

Another problem with the conventional sanitary napkin is that the pad is too wide to properly fit between the woman's thighs, such that the pad is often uncomfortable.

The present invention relates to a sanitary napkin wherein the pad portion of the napkin is completely encapsulated within a thin sheet of liquid impermeable material, whereby menstrual blood and other secretions are fully retained within the pad material; the menstrual liquids are prevented from contacting the woman's skin, thereby minimizing the risks of infection.

In a preferred embodiment of the invention the napkin comprises an elongated absorbent pad having a narrow section adopted for placement between a woman's thighs and a wide section adopted for placement against the woman's abdomen. The narrow section can have a transverse width of about one inch, whereas the wide section can have a transverse width of about two and one half inch. The shape of the pad is such that the pad is quite comfortable while it is being worn; the narrow section of the pad conforms to the woman's anatomy, without binding or rubbing against the woman's skin. The wide section of the pad lying against the woman's abdomen provides an adequately sized reservoir for menstrual blood and other secretations.

As an important feature of the invention, the sanitary napkin comprises a liquid absorbent plug extending right angularly from the narrow section of the pad for insertion into the woman's vagina. The plug is contiguous with the pad, whereby menstrual blood can flow through the plug into the pad for collection and distribution to other parts of the pad not in direct contact with the plug.

The aforementioned thin sheet of liquid impermeable material extends entirely around the porous pad, but not around the plug, so that menstrual fluids are prevented from leaking outwardly through the pad surface. Since the plug is located within the woman's vagina, there is a relatively unobstructed path for liquid flow through the plug into the porous pad.

A major feature of the invention is the complete containment of the menstrual liquids, with no possibility for the depositing of such liquids on the woman's skin. The pad can be designed to have a relatively large total volume, to provide an adequately sized reservoir for the collecting liquids.

THE DRAWINGS

DESCRIPTION OF A PREFERRED EMBODIMENT OF THE INVENTION

Figure 1:
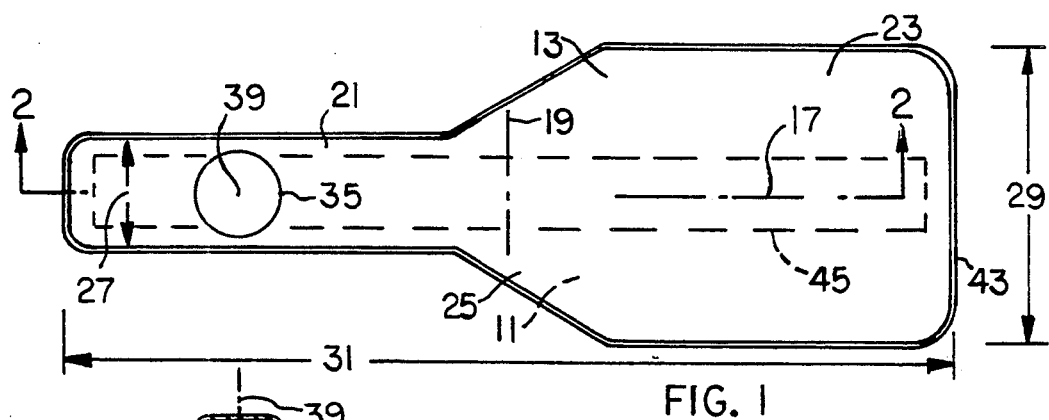
FIG. 1 is a plan view of a sanitary napkin constructed according to the invention.
Figure 2:
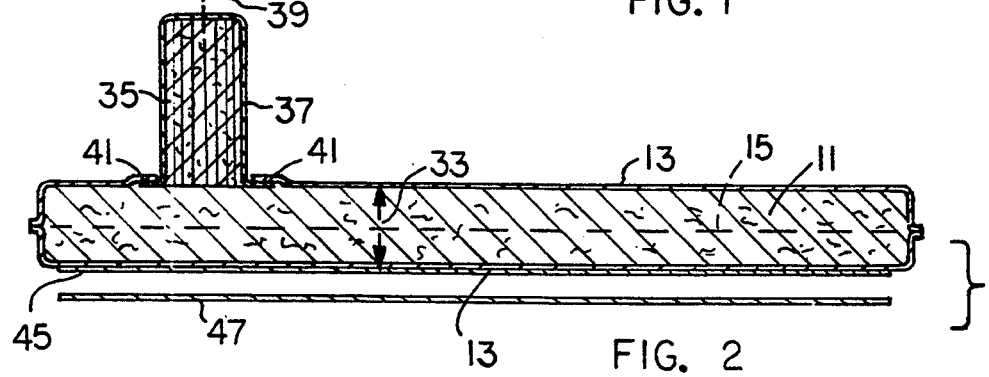
FIG. 2 is a sectional view taken on line 2—2 in FIG. 1.

FIGS. 1 and 2 of the drawings show a sanitary napkin that comprises a liquid absorbent pad 11 formed of cotton batting. The cotton fibers are frictionally interconnected and compressed together so that the pad retains a given shape while being sufficiently flexible to conform to a woman's anatomy. Pad 11 is encapsulated within a liquid impermeable covering 13, said covering being formed of two thin flexible sheets of a vinyl plastic material having peripheral edge areas thereof heat sealed together on a parting line (or plane) designated generally by numeral 15.

Pad 11 has a longitudinal axis 17 and a transverse axis 19. As shown in FIG. 1, the encapsulated pad has a narrow section 21, a wide section 23, and a flared connector section 25. The transverse width dimension 27 of the narrow section may be about one inch, whereas the transverse width dimension 29 of the wide section 23 may be about two and one half inch. The wide and narrow pad sections 21 and 23 may each be about three inches long. The total length dimension 31 of the encapsulated pad may be about eight inches. Pad 11 has a preferred thickness dimension 33 measuring about five eighth inches.

Projecting right angularly from the upper face of pad 11 is a cylindrical plug 35, said plug being formed of compressed cotton batting having a cotton gauze sheath 37 overlying its exposed surface, i.e. its upper end surface and its cylindrical side surface. The cotton batting for plug 35 can be a thin flat strip of cotton batting wound in spiral fashion generally around the plug central axis 39. Alternately the cotton batting can be a solid cylindrical mass of cotton fibers compressed together in a suitable mold cavity. The cotton gauze sheath 37 is telescoped over and around the cylindrical plug to prevent the cotton batting fibers from separating from the plug body.

Cotton gauze sheath 37 has outurned flanges 41 adhesively attached to the surface of cotton pad 11. During or prior to adhesive attachment of flanges 41 to the pad 11 surface the cloth-covered plug is pressed firmly against the pad surface so that the lower end face of the cotton plug has firm pressure contact with the pad surface. The plug of cotton batting is thus contiguous with the cotton pad, whereby menstrual blood can flow freely through the plug into the pad by wetting and saturating the cotton fibers, and by capillary flow through the pores within the plug and pad.

The aforementioned liquid impermeable covering 13 is applied to pad 11 after attachment of porous plug 35 to the pad upper surface. One of the vinyl sheets (for covering 13) has a small cylindrical hole there through for fitting around the cylindrical side surface of the plug. Each vinyl sheet has thickness on the order of a conventional sheet of paper, e.g. about 0.002 inch, whereby the encapsulated pad is flexible while being sealed against outflow of blood and other menstrual liquids through the pad surfaces.

The sanitary napkin is used or applied by the woman so that the porous cylindrical plug 35 is inserted into the woman's vagina. The narrow section 21 of the encapsulated pad is placed between the woman's thighs, and the wide section 23 of the encapsulated pad is placed against the woman's abdomen. Wide section 23 of the pad will extend generally upwardly along the abdomen so that end 43 of the pad is uppermost. Flared connector section 25 of the pad (between sections 21 and 23) serves as a transition section to avoid sharp side edges that might be uncomfortable to the woman.

A feature of the invention is that the narrow section 21 of the encapsulated pad fits comfortably between the woman's thighs, without binding, folding or rubbing against the woman's skin. The wide section 23 of the encapsulated pad forms an adequately sized reservoir for collecting the menstrual liquids, thereby avoiding any backflow or liquid limitations that could pose a bealth or infection problem.

As previously noted, the liquid impermeable covering entirely surrounds the porous pad 11, so that the collected menstrual liquids are prevented from leaking out of the pad or otherwise coming in contact with the person's skin. This is advantageous in that menstrual deposits on the skin surface are avoided, with a lessened risk of infection that such deposits might cause. Also, the woman does not experience a wet condition on her skin that can be somewhat uncomfortable, and that can produce a sense of uneasiness.

In order to better retain the sanitary pad on the women's body, the pad is provided with an elongated (or film) strip 45 of contact adhesive on the lower surface of the pad; i.e. the pad surface facing away from plug 35. As shown in FIG. 1, adhesive strip (film) 45 extends substantially to the entire length of the encapsulated pad. The woman can put on a conventional underpants after (or during) placement of the sanitary napkin on her body; adhesive strip 45 will adhere to the adjacent interior surface of the underpants, such that the underpants will retain and hold the sanitary napkin in its desired location.

For packaging purposes a peel-off strip of paper 47 will be applied to the adhesive film 45. Prior to using the napkin the woman will remove the protective strip of paper from the napkin.

The length and diameter of plug 35 can be varied within limits while still achieving the objects of the invention. In a preferred form of the invention the cylindrical plug will have an axial length of about one and one half inches, and a diameter of about three quarter inch.

Figure 3:
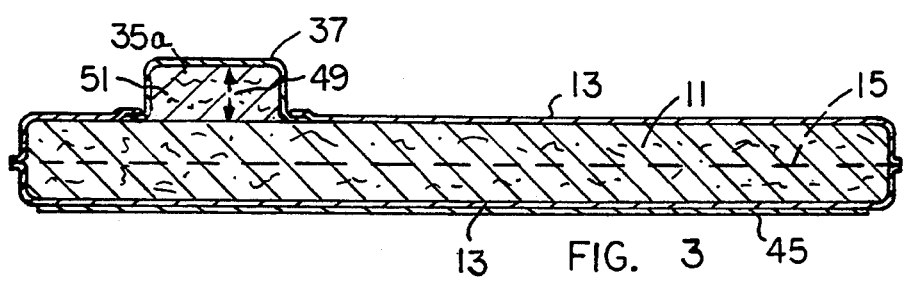
FIG. 3 is a view taken in the same direction as FIG. 2, but illustrating another embodiment of the invention.

FIG. 3 shows a variant of the invention designed for use by younger woman, who experience only a relatively slight menstrual flow. In this case the vaginal-insertional plug 35a has a reduced thickness dimension 49. The plug need not be cylindrical. It can have an oblong cross-section while still fitting within the vagina, since the plug fits only into the mouth of the vagina and can reform the vagina wall to fit around the plug side surface without causing the woman any discomfort. Even though the porous plug extends only a short way into the vagina it can still form a liquid seal to confine the menstrual liquid flow to a path extending through the porous plug into the cotton pad 11.

Plug 35a is comprised of a solid oblong block of cotton batting 51 having a cotton gauze sheath 37 on its exposed surfaces. The plan dimension of the FIG. 3 napkin is as shown in FIG. 1.

Figure 4:
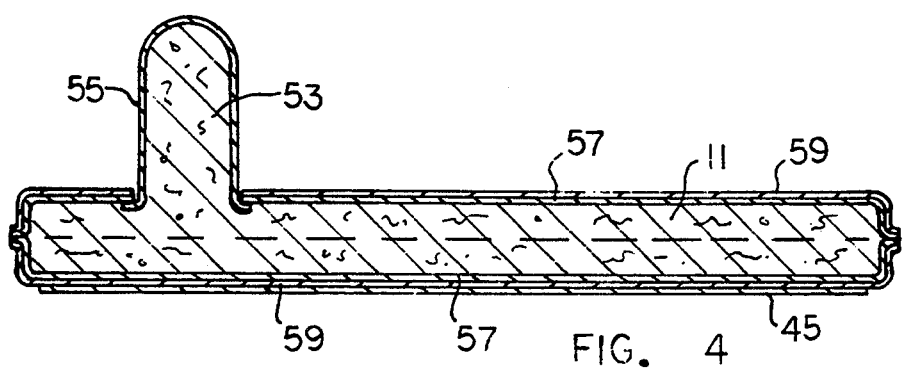
FIG. 4 is a longitudinal sectional view taken through a third embodiment of the invention.

FIG. 4 shows a variant of the invention wherein the cotton plug 53 is formed integrally with the cotton pad 11. Thus, the plug and pad comprise a unitary continuous mass of cotton compressed to the illustrated configuration, whereby menstrual liquids can flow through the plug into the pad, with minimal flow resistance.

Cotton plug 53 can be located within a tubular sock 55 formed of an absorbent knitted material commonly used for conventional wash cloths. This knitted material is porous and absorbent, such that when it is used as a sheath around cotton plug 53 the menstrual liquids are readily absorbed and transported through the plug into cotton pad 11. The plug preferably has a cylindrical side surface.

In the FIG. 4 sanitary napkin, cotton pad 11 is encapsulated within a multi-layer covering. The inner layer of the covering comprises a cloth sheet 57 formed out of an absorbent porous material, preferably the same knitted material that is used for tubular sock 55. The outer layer of the covering may be a film of plastic material 59 laminated onto the outer surface of cloth layer 57. Plastic film 59 can be a vinyl plastic material sprayed onto one face of the cloth material prior to cutting the cloth sheet to its desired size.

The multi-layer covering around cotton pad 11 can comprise two multi-layer (plastic-coated) sheets having their peripheral edges stitches together, or adhesively connected together, to form a liquid impermeable covering around the cotton pad.

The inner knitted cloth layer in conect with cotton pad 11 is used for the purpose of channeling menstrual liquid along and around the cotton material to remote areas of the cotton pad. Thus, the porosity of the cloth sheet in contact with cotton pad 11 is relatively great so that menstrual liquids flow readily along the cloth material, whereby all surface areas of the pad can be supplied with menstrual liquids. The plan configuration of the FIG. 4 napkin is as shown in FIG. 1.

The drawings show particular forms and configurations that the invention can take. However, it will be appreciated that the invention can be practiced in various forms and configurations.

What is claimed is:

1. A sanitary napkin comprising:
a liquid-absorbent pad having a longitudinal axis and a transverse axis; said pad having a narrow rectangular section adapted for placement between a woman's thighs without folding, a wide section adapted for placement against the woman's abdomen, and a flared connector section interconnecting said narrow and wide sections;

a liquid-absorbent plug projecting from the narrow section of the pad for insertion into a woman's vagina; said plug comprising a plug body formed of cotton batting, and a porous sheath overlying said plug body, said sheath having a flange fitting against the liquid-absorbent pad;

said plug being contiguous with said pad whereby menstrual fluids can flow through the plug into the pad;

a porous cloth sheet (57) surrounding said liquid-absorbent pad for channeling menstrual fluids along and into the pad; said cloth sheet fitting around said plug to overly the plug flange;

and a liquid impermeable covering extending entirely around said pad and porous cloth sheet, but not around said plug; said liquid impermeable covering having an opening that fits around the plug so that the covering fully encapsulates the absorbent pad and cloth sheet.

* * * * *